United States Patent [19]

Pulli et al.

[11] 4,126,438

[45] Nov. 21, 1978

[54] NOVEL GOLF TEE

[76] Inventors: Michael A. Pulli, 1279 Schwab Rd., Hatfield, Pa. 19440; James E. Bruno, 8303 Strahle Pl., Philadelphia, Pa. 19111

[21] Appl. No.: 723,508

[22] Filed: Sep. 15, 1976

[51] Int. Cl.² .......................................... A01N 17/08
[52] U.S. Cl. ............................................ 71/3; 71/24; 71/64 SC; 71/65; 71/79; 71/DIG. 1; 273/33; 273/212; 47/48.5
[58] Field of Search .................. 71/1, 3, 11, 23, 24, 71/64 SC, 64 E, 64 P, 64 G, 65, 79, DIG. 1; 273/33, 202–212; 47/48.5

[56] References Cited

U.S. PATENT DOCUMENTS

| | | | |
|---|---|---|---|
| 1,645,001 | 10/1927 | Hodges | 71/23 X |
| 3,502,458 | 3/1970 | Schenk | 71/64 R |
| 3,884,479 | 5/1975 | Gordas | 71/64 F |
| 3,954,263 | 5/1976 | Whelan et al. | 71/64 F X |

FOREIGN PATENT DOCUMENTS

7,100,620   8/1971   Japan ........................................... 71/23

*Primary Examiner*—Ferris H. Lander
*Attorney, Agent, or Firm*—Joseph W. Molasky

[57] ABSTRACT

A disintegrable golf tee comprised of clay, grass seed and a soil conditioner selected from among the following ingredients: a fertilizer, insecticide, herbicide, fungicide, larvacide or a mixture of same.

Humus may be added to the composition as an optional ingredient.

The tee thus produced can be shattered upon impact with a club head or it can be impressed into the ground. In either event, it decomposes upon contact with moisture to impart beneficial properties to the grass and soil.

4 Claims, No Drawings

NOVEL GOLF TEE

This invention relates to a golf tee which shatters on impact and which decomposes in the presence of moisture to impart beneficial effects to the grass and soil.

Golf tees comprised of wood and plastic often splinter when struck with a club at high velocity and this creates a litter problem.

This invention not only overcomes the litter problem associated with wooden and plastic tees but, in addition, it provides a means for converting the tee or its remnants into a valuable soil conditioner. In addition, it provides a means for seeding the playing area so as to keep it in good repair.

If the tee of this invention is not shattered it can be impressed, in its entirety, into the ground where it will disintegrate and provide filler, seed, nutrients, a herbicidal agent, an insecticide, larvacide, fungicide, or other conditioner to the soil.

The tee of this invention is also economical to produce. It has the same appearance as a conventional tee and it can be painted or lacquered to provide an enameled or shiny surface which appeals to the most discriminating golfer.

BACKGROUND OF THE INVENTION

Disintegrable gold tees are known in the art. Indeed, it is well known to manufacture tees comprises of sand and a binding agent which holds the material together so that it can be shaped and maintained in the desired structure.

It is also known to incorporate grass seed and fertilizer into said tees for the purpose of providing the soil with the nutrients and means needed to invigorate the teeing grounds.

Unfortunately, however, the binding agents which are generally used in gold tee compositions are viscous and sticky substances. And although such agents can be dehydrated to provide a dry tee, nevertheless, upon coming into contact with moisture, the said agents are rehydrated and resume their sticky state. As a consequence, they create an unsatisfactory condition because the rehydrated binder will sometimes adhere to the ball or club and otherwise render the course unsuitable for play.

Furthermore, there are no tees available which, in addition to decomposing into the soil, also combat fungi, weeds, larvae and soil dwelling insects.

In U.S. Pat. No. 1,152,649 there is described a water soluble tee which is typical of the known disintegrable tees. That patent relates to a colorless, transparent, water soluble gold tee which utilizes common gelatin as the binding agent. Similar tees utilizing gelatinous and nitrogenous binding agents are also disclosed in U.S. Pat. No. 1,645,001 and in U.S. Pat. No. 1,176,039.

The disadvantage to tees comprised of gelatin and nitrogenous binders lies in their tendency to soften and become tacky in damp or humid weather. And in actual play, as indicated above, there is a tendency for the gelatinous material to adhere to the club head or to the ball and, to a certain extent, to the playing surface.

An alternative tee is described in U.S. Pat. No. 702,078. That patent describes the use of flour and molasses as a binder for clay and sand in preparing a disintegrable tee. However, again, in hot or wet weather the said tee has a tendency to soften and, therefore, it exhibits the same undesirable properties as the gelatinous or nitrogenous tees.

A variation on the disintegrable tee is described by W. McLeod in U.S. Pat. No. 1,815,520. McLeod, however, eschews the use of fertilizer as a component in tee comcompositions. Indeed, this patent indicates that it is unsatisfactory to incorporate any ingredients into the tee other than clay and water. Furthermore, the McLeod patent is directed to tees of a frustoconical shape and, therefore, it bears no resemblance to the peg tee which is in vogue today.

One difficulty in producing a disintegrable tee lies in the fact that a balance must be struck between ostensibly competing needs. Thus, for example, the composition of said tee must be of such density as to lend itself to molding procedures while, at the same time, it must possess a capacity for absorbing water so that it can be decomposed by natural means. Celluloid, rubber and plastics have been used for this purpose but the results have been disappointing because, while they provide excellent structural properties, they are not affected appreciably by moisture and, therefore, they do not decompose readily over the short-term.

One disadvantage to disintegrable tees containing fertilizers has been the uneven supply of nutrients which they provide to the playing area. Indeed, golf tees comprised of fertilizers generally release their nutrients quickly and in localized spots and thus fail to provide the slow release and even distribution which is needed for proper feeding. The result is an over-greening effect, in small areas, and this produces a patchwork-type effect on the teeing surface.

THE INVENTION

It is an object of this invention to describe a novel golf tee which disintegrates into the soil to provide filler, seed, nutrients, herbicides, fungicides, insecticides, larvacides and other beneficial ingredients thereto.

Another object is to describe a gold tee composition in which the binding agent will disintegrate into the soil without forming a sticky or viscous residue.

Still another object is to describe a novel gold tee comprised of clay and decayed vegetable matter for the purpose of providing carbon, oxygen and nitrogen to the soil.

A still further object is to provide a tee with an outer film or coating which protects the said tee from flaking or rupturing and which also serves as a slow-release means for the emission of nutrients or other beneficial ingredients into the soil upon contact with moisture.

The objects of this invention are achieved by forming the tee from naturally occurring clays, particularly those containing a high percentage of kaolinite, halloysite, montmorillonite or illite. Illustrative of such clays are, for example, bentonite or bleaching clays and the like.

In its broadest aspects, this invention relates to golf tees comprised of clay, grass seed and a soil conditioner. Soil conditioners include, for example, lawn fertilizers, herbicides, fungicides, larvacides and insecticides or a mixture of same.

According to another aspect of this invention the said tees may also be comprised of decayed vegetable matter such as humus. The humus imparts a more plastic state to the largely clay composition and provides a means of adding nitrogen, carbon and oxygen to the soil.

The tee compositions of this invention are highly suitable for compacting and they can be used equally well in low compression or sudden impact molding.

The tees thus produced are homogeneous in appearance and have a dense and smooth outer surface. The molding and stamping step imparts a shell-like exterior to the tee which renders it only slightly absorbent to moisture; but, the interior of said tee is coarse and irregular and highly absorbent.

In general, tees containing humus do not possess the shell-like effect or dense outer surface which characterizes those tees comprised solely of clay, seed and soil conditioner. Therefore, in the case of humus-containing tees it may be desirable to spray the outer surface with a lacquer, paint or enamel so as to maintain the integrity of the tee and prevent it from flaking or becoming broken prior to its actual use.

In addition to preserving the tee, the spray coating also serves as a means for controlling the release of the soil conditioning agent into the soil.

As an alternative to coating the outer surface of the tees, they may be fired at temperatures in the range of from about 450°-600° C., preferably, at temperatures of 500°-600° C.

The firing step produces a protective covering on the outer surface of the tee and renders it more resistant to the solvent action of water and less likely to flake or rupture during shipment or use.

Tees which are heat dried at temperatues below 375° C. do not differ appreciably from air-dried tees. The latter, absent any lacquer, paint or enamel coating, decompose much more readily and are more easily ruptured than tees subjected to the firing step.

The soil conditioning agents which are utilized in the present compositions include any of the commonly available nutrients and soil modifiers. These include not only growth-promoting agents such as fertilizers but, also, substances which protect or strengthen the soil or plant against fungi, molds, naturally occurring diseases or insect infestation and the like. Therefore, it is comtemplated to employ as an additive in the instant compositions such materials as weed killers, insecticides, larvacides and fungicides, as well as those nutrients and fertilizing substances commonly referred to as growth promoters.

The precise proportions of ingredients comprising the tee is not critical and, indeed, the amount of clay, seed, soil conditioner and humus utilized may vary within wide limits. However, it is essential that clay be present in a major amount because it serves as the structural base for shaping the tee and maintaining it as an integral unit.

In practice, in formulating the instant tee, clay is added to a suitable solvent such as water or an alcohol and the suspension is mixed to a plastic mass. A soil conditioner, grass seed and, optionally, humus, is added to the suspension and the mass is mixed thoroughly to provide a homogeneous composition.

Thereafter, the composition is either impact molded or poured into tee-molds and the solvent medium is evaporated by natural means or by the application of heat so as to render the composition anhydrous.

Having set forth the broad limits of this concept, the invention will now be described by reference to specific embodiments. However, it is to be understood that the embodiments and examples which follow are illustrative only and are not intended to be limitative.

Consequently, any variation from this invention which amounts to no more than a change in the proportions of ingredients or the substitution of one functionally equivalent ingredient for another, is considered as being within the scope of this invention and not a departure therefrom.

EMBODIMENTS

In practicing this invention a clay such as Bentonite, or bleaching clay, is ground to a fine powder and added to an aqueous media to afford a colloidal clay suspension. This addition is usually conducted with stirring to assure that the clay particles are thoroughly suspended in solution. The amount of clay added to the water is not critical but, in general, it is advisable to utilize 1-2 parts of clay for every 2-3 parts of water. However, in a preferred embodiment of this invention, the clay and water are mixed in equal proportions.

Alternatively, in lieu of water, an alcohol such as ethanol or propanol, may be substituted therefor with equally good results. For economy reasons, water is the preferred medium in producing the instant tees but, in certain instances as, for example, where the tees are air-dried and a rapid evaporation of solvent is desirable, alcohol may be utilized with no sacrifice in the quality of the tee.

After stirring the colloidal clay to a homogeneous and pasty mass, grass seed and a soil conditioner such as fertilizer or a fungicide, larvacide or insecticide is added to the mixture and stirring is resumed.

The amount of clay comprising said mixture is not critical but, as a general rule, it is desirable to employ from about 55-75% clay, about 15-35% soil conditioner and from about 5-15% seed. In a preferred embodiment of this invention the proportions of ingredients are formulated as follows: the clay comprises from about 60-70% of the composition, but, most preferably, 65%; the soil conditioner is present in an amount of from about 20-30% but, most preferably, 25%; and the grass seed comprises from about 5-15% of said mixture but, most preferably, 10%.

Once the colloidal clay and soil conditioner have been thoroughly mixed the plastic mass is poured into the tee molds and the latter are dried thoroughly in the open air at ambient temperature.

Alternatively, the tee molds can be dried in a closed system at temperatures in the range of from about 60°-425° C. By operating at elevated temperatures it is possible to reduce the drying time appreciably so that the said molds can be reused in a continuous tee-manufacturing operation.

When drying the tee molds it is essential that extremely high temperatures be avoided because the texture of the clay and its colloidal characteristics can be destroyed if the temperature exceeds a range of 725°-775° C. Therefore, if the present molds are dried by firing it is most desirable to maintain the firing temperature below 725° C. and, preferably, within the range of from about 450°-600° C. Tees fired within this range possess greater strength than air-dried tees. Conversely, air dried tees are more easily disintegrated than fired ones.

Compositions comprised solely of clay and soil conditioner lend themselves to sharp impact molding rather than slow compression. The consistency required in the clay composition to achieve a sharp mold will vary with the type of clay employed but, as a practical matter, colloidal clays having a water content of from about 15–25% generally afford good results. Such compositions require an energy equivalent of from about 4 foot pounds to 18 foot pounds to achieve effective impacting and a high quality tee.

A second embodiment of this invention consists of adding decayed vegetable matter such as humus to the tee composition. According to this procedure, the colloidal clay is formulated according to the method previously described, that is, by adding clay in finely powdered form, to a solvent, such as water or alcohol, and the suspension is mixed thoroughly. Thereafter, humus is added to the colloidal suspension, with mixing, followed by the addition of seed and soil conditioner. The entire mixture is agitated until the composition assumes the appearance of a homogeneous and pasty mass.

The homogenized mixture of clay, humus, seed and soil conditioner is poured into tee molds and dried for several hours. The said molds can be air dried at ambient temperature or they can be dried at raised temperatures in the range of from about 26°–100° C. Alternatively, the tee molds can be placed in a drying oven and subjected to temperatures in the range of from about 60°–425° C. for a shorter interval.

Tees comprised of humus do not lend themselves to sudden impact molding and, therefore, such tees are most generally formed by slow compression means and static molding. Also, tees comprising humus have a coarse and more spongeous texture than tees comprised solely of clay, seed and soil conditioner. They absorb water more readily and, in general, they decompose and surrender their beneficial ingredients to the soil with greater ease than tees absent humus. And because humus is comprised of carbon, oxygen and nitrogen the tee containing same imparts these life-supportive ingredients to the soil.

The disadvantage to the humus-containing tee lies in its tendency to flake and rupture more easily than tees comprised solely of clay, seed and soil conditioner.

This tendency can be overcome by spray-coating the said tee with a paint, lacquer or enamel composition. The spray-coating creates a shell-like outer surface on the tee which renders it less likely to chip, flake or fracture prior to use. Also, it serves as a means for controlling the decomposition and release of active ingredients into the soil. The spray-coating also has a more visible effect. It gives the tee an aesthetically pleasing appearance and a texture which is pleasant to the touch.

In a variation of this invention we have found that a water soluble fertilizer can be dissolved in a waterbased or latex paint and the resulting mixture can be sprayed onto the humus-containing tee in the same manner as with conventional paints. The tee thus coated has a shell-like outer surface which, in addition to providing color, also provides it with a water soluble surface which reacts with the moisture in the soil to immediately impart nutrients thereto. A water-soluble fertilizer which may be used for this purpose is a 30-10-10 mixture of nitrogen, phosphoric acid and potash. One tablespoon of this fertilizer dispersed thoroughly in one gallon of a latex paint provides a suitable composition for spray-coating purposes.

The amount of humus which is employed in formulating the humus-containing tee of this invention is not critical and, in general, it is only necessary that the clay be present in a major amount. However, in practice, we have found it desirable to employ compositions comprising from about 40–60% clay, 10–30% humus, 10–30% soil conditioner and 5–15% seed.

A preferred embodiment relates to a tee composition consisting essentially of from about 45–55% clay, 15–25% humus, 15–25% soil conditioner and 5–15% seed.

An additional embodiment, and one which we have found to be particularly suitable in producing humus-containing tees consists essentially of 50% clay, 20% humus, 20% soil conditioner and 10% seed.

The fertilizers, fungicides, insecticides, larvacides and other active ingredients which are added to the tee-forming compositions of this invention are any of the well-known growth promoting and soil conditioning agents.

The fertilizer ingredients include compositions rich in nitrogen, phosphoric acid and potash. Typical of these is the following:

Nitrogen: 20%
    14.39% Ammoniacal Nitrogen
    5.61% Nitrate Nitrogen
Phosphoric Acid ($P_2O_5$): 20%
Potash ($K_2O$): 20%

Insecticidal agents which may be utilized include octahydro-methano-tetrahydroindane (Chlordane; Dow Chemical Company), hexachloro-epoxy-octahydro-dimethanonaphthalene (Dieldrin; Dow Chemical Company), dimethyl-trichlorophenylphosphorothioate (Korlan; Dow Chemical Company) and O,O-dimethyl-(2,2-dichlorovinyl)phosphate (DDVP: Shell Chemical Company).

Herbicidal agents having pre-emergence and post-emergence activity are well known in the art and these may be formulated into the instant tee-compositions in the herein-described manner. Typical of said herbicides are the 1,2,3 thiadiazol-5-ly-ureas described in U.S. Pat. No. 3,874,873. One such herbicidal agent which has proved particularly effective is 1-methyl-3-(4-isopropyl-carbamoyl-1,2,3-thiadiazol-5-yl)urea. That agent is a selective herbicide which possesses pre-emergence and post-emergence activity against crabgrass and mustard.

Another herbicide which may be utilized is 1,1-dimethyl-3-(4-isobutylcarbamoyl-1,2,3-thiadiazol-5-yl)-urea. This compound has a wide spectrum of activity and has been found useful as a post-emergent herbicide against green fox tail grass (*Setaria viridis*), barnyard grass (*Echinochloa crusgalli*), velvet leaf (*Abutilon theophrasti*), crabgrass (*Digitaria sanguinalis*), annual morning-glory (*Ipomoea purpurea*) and Johnson grass (*Sorghum halepense*).

Other active agents, such as larvacides and fungicides, may also be added to the tee-forming compositions of this invention in effective amounts. It is not the intention of this invention to claim these active ingredients per se and, therefore, the use of any agricultural ingredients which have been proven effective in its growth-promoting properties and soil-conditioning effects are utilizable in this invention.

The tee of this invention may conform to any configuration which is suitable for maintaining a golf ball in position for play. One such tee consists of a tapering stem and a concave head upon which a golf ball can be placed. The stem of this tee terminates in a tip which is impressed into the ground and, left unattended, it can stand in an upright position with its concave head facing upwards. Such tees are in common use today and its design is particularly suitable for this invention because when the tip thereof is impressed into the ground it loosens the earth and prepares it for the seeds and conditioning agents which are sought to be dispersed into the soil. This particular tee is referred to herein as a peg tee.

The tee described in the preceding paragraph is a preferred design for the tee of this invention, but it is to be understood that this concept is not limited to a tee of any precise shape or size. Indeed, the tee of this invention may be of any suitable design as, for example, in the form of a truncated cone. In this embodiment the base of the tee if flat and is adapted for placement on the green without any impression being made on the green or teeing surface. However, the upper surface of this tee is saucer-shaped or concave and, in this respect, it is similar to the peg tee which constitutes the preferred embodiment of this invention.

The following examples illustrate the tee of this invention and the means by which it can be produced. However, it is to be understood that the examples are illustrative only and are not intended to be limitative.

EXAMPLE 1: Clay-Seed-Fertilizer

A finely powdered clay (65 parts) is put into a receptacle and water is added slowly, with mixing, until the water content of the mixture reaches a level of 50% by volume.

The aqueous mixture is thoroughly blended for thirty minutes to afford a homogeneous suspension which is in the form of a pasty mass. A lawn fertilizer (25 parts) comprising 14.39% ammoniacal nitrogen, 5.61% nitrate nitrogen (Total nitrogen: 20%), 20% phosphoric acid and 20% potash is added to the mixture slowly, with stirring. The composition, comprising 65% clay and 25% fertilizer by weight, is then blended thoroughly at room temperature for twenty minutes to assure a thorough distribution of the fertilizer. Grass seed (10 parts) is slowly added, with mixing, and the blending is continued for an additional 30 minutes.

After the blending step has been concluded, the mixture is poured into golf tee molds and said molds are fired at 450° C. for 25 minutes.

Upon termination of the firing step the tees are taken from the molds and placed onto trays where they are allowed to come to room temperature. The tees thus produced are in a condition suitable for immediate use.

EXAMPLE 2: Clay-Seed-Fertilizer-Humus

A variation on the clay, seed and fertilizer containing tee of Example 1 includes the use of humus as an ingredient in the tee composition. According to this embodiment the procedure of Example 1 is employed but the following ingredients are substituted for those recited therein: clay (50 parts), fertilizer (20 parts), humus (20 parts) and seed (10 parts).

Upon termination of the firing and cooling steps there are thus obtained golf tees comprised of clay, seed, fertilizer and humus which are suitable for immediate use.

EXAMPLE 3: Clay-Seed-Humus-Herbicide

Bentonite (50 parts), finely bolted, is added to an equal amount of water by volume and the composition is thoroughly mixed.

A mixture of humus (20 parts; containing humic acid) and grass seed (10 parts) is added, with stirring, to the colloidal mixture of bentonite and water.

The resulting mass is blended for 35 minutes and the herbicide, 1-methyl-3-(4-isopropylcarbamoyl-1,2,3-thiadiazol-5-yl)urea (20 parts), is added slowly with mixing.

Upon termination of the mixing step there is thus obtained a homogeneous mass consisting of 50% bentonite, 20% humus, 20% herbicide and 10% grass seed. The said mixture is then poured into golf tee molds and air-dried for twelve hours at room temperature.

Upon termination of the drying step the tees are removed from the molds and are spray-lacquered and allowed to dry. The finished product is a golf tee with a thin outer coating which, over a period of several days, will decompose to provide a slow release of carbon, oxygen, nitrogen, humic acid and an herbicide to the soil. This herbicide has a selective pre-emergence and post-emergence effect against crabgrass.

EXAMPLE 4: Clay-Seed-Humus-Fertilizer-Insecticide

Bleaching clay (45 parts), finely divided, is added to an equal amount of water by volume, with mixing. The colloidal suspension is mixed thoroughly for an additional 15 minutes to afford a homogeneous and pasty mass.

A mixture of humus (15 parts), grass seed (10 parts), a fertilizer comprising 30% nitrogen, 10% phosphoric acid and 10% soluble potash (15 parts) and the insecticide O,O-dimethyl-(2,2-dichlorovinyl)phosphate (15 parts), are added, with stirring, to the mixture of bleaching clay and water.

The resulting mass is mixed for forty minutes to provice a homogeneous mixture.

After the mixing step has been concluded, the mixture is poured into golf tee molds and the latter are placed into a drying oven where they are dried at 425° C. for 30 minutes.

Upon completion of the drying step the anhydrous tees are removed from the molds and spray coated with a white enamel. When the enamel finish has dried the resulting tees are in a condition suitable for use. The insecticidal agent in the tees thus produced has the ability to kill the following insects: clover mites, springtails, gnats, dog ticks and carpet beetles.

By substituting other, known, soil-conditioning and, growth-promoting agents for the fertilizer and insecticidal agents set forth in Example 4, supra, and otherwise following the procedure described therein, other disintegrable tees can be produced.

What is claimed is:

1. A golf tee which decomposes in the presence of moisture and to which a water soluble coating containing a water soluble fertilizer has been applied, consisting essentially of a homogeneously blended mixture of clay, grass seed, humus and a soil conditioner selected from the group consisting of a fertilizer, herbicide, fungicide, larvacide, insecticide and mixtures thereof.

2. A golf tee according to claim 1 in which the water soluble coating contains a mixture of a water soluble herbicide and a water soluble fertilizer.

3. A golf tee which decomposes in the presence of moisture and to which a water soluble coating containing a water soluble fertilizer has been applied, consisting essentially of a homogeneously blended mixture of clay, grass seed and a soil conditioner selected from among a fertilizer, fungicide, larvacide, insecticide and mixtures thereof.

4. A gold tee according to claim 3 in which the water soluble coating contains a mixture of a water soluble herbicide and a water soluble fertilizer.

* * * * *